(12) United States Patent
Amini

(10) Patent No.: US 12,064,144 B2
(45) Date of Patent: Aug. 20, 2024

(54) PIVOTING SPINAL SCREW

(71) Applicant: Aminullah Amini, Potomac, MD (US)

(72) Inventor: Aminullah Amini, Potomac, MD (US)

(*) Notice: Subject to any disclaimer, the term of this patent is extended or adjusted under 35 U.S.C. 154(b) by 218 days.

(21) Appl. No.: 17/704,640

(22) Filed: Mar. 25, 2022

(65) Prior Publication Data

US 2023/0301687 A1 Sep. 28, 2023

(51) Int. Cl.
*A61B 17/70* (2006.01)
*A61B 17/56* (2006.01)
*A61B 17/86* (2006.01)

(52) U.S. Cl.
CPC ...... *A61B 17/7035* (2013.01); *A61B 17/7032* (2013.01); *A61B 17/7092* (2013.01); *A61B 17/8625* (2013.01); *A61B 2017/564* (2013.01)

(58) Field of Classification Search
CPC ............ A61B 17/7032; A61B 17/7035; A61B 17/7092; A61B 17/8625; A61B 17/8685; A61B 2017/564
See application file for complete search history.

(56) References Cited

U.S. PATENT DOCUMENTS

| | | | | |
|---|---|---|---|---|
| 2008/0255618 A1* | 10/2008 | Fisher | ................ | A61B 17/7064 606/301 |
| 2014/0163624 A1* | 6/2014 | Siegal | ................ | A61B 17/7032 606/304 |
| 2018/0168539 A1* | 6/2018 | Singh | .................. | A61B 8/4483 |

* cited by examiner

*Primary Examiner* — Nicholas J Plionis
(74) *Attorney, Agent, or Firm* — Michael L. Greenberg, Esq.; Greenberg & Lieberman, LLC

(57) ABSTRACT

A surgical spinal screw apparatus configured to facilitate safer spinal surgery and reconstruction via a pivoting tip. The apparatus is equipped with a tip which is configured to pivot about a pivot point which facilitates minor redirection of the apparatus when driven through bone such as a vertebra. The apparatus is geared towards finding a path of least resistance through the bone. As such, the tip is configured to pivot towards less dense pockets of bone as the screw is placed during surgery. A pedicle finder, a companion apparatus, is configured to facilitate placement of the spinal screw, and is similarly equipped with a pivoting tip. The spinal screw is threaded and is equipped with a hollow core to facilitate the passage of a guide wire to assist in placement and tension of the pivoting tip as needed.

16 Claims, 5 Drawing Sheets

PIVOTING SPINAL SCREW

FIELD OF THE PRESENT INVENTION

The present invention relates to the field of medical practice, and more specifically relates to a surgical spinal screw and pedicle finder configured to facilitate safer spinal surgery via a pivoting screw tip and pivot point pedicle finder.

BACKGROUND OF THE PRESENT INVENTION

Every year, a number of individuals require spinal surgery. For example, spinal fusion surgery is known to require at least one spinal screw. The procedure, as with most surgery, has risks. Nerve damage and other complications can occur, even with the most skilled surgeons performing the procedure.

Unfortunately, there are presently few ways available to mitigate these risks. The spinal screws presently in use have no features which enable them to more safely navigate the bone of the subject. The correct position and safe placement of a screw is not confirmed until after the patient has left the operating room, and the surgeries are finished. However, vertebral bone has a very thick cortical outer shell as well as a soft inner cancellous portion which could create a sfe entry into the path of least resistance for the screw. If there were a way in which a surgeon could be more confident in knowing the screw was optimally positioned and was placed into the bone in a path of least resistance, some risk to bone and nerve damage could be mitigated.

Thus, there is a need for a new form of spine surgical screw which is equipped with a pivoting tip. Such a tip of the surgical screw is preferably able to shift the path of the screw as it is positioned in order to achieve a more optimal placement of the screw via a path of least resistance within the bone. Such a pivoting surgical screw is preferably accompanied by a pedicle finder similarly equipped with a pivoting point to facilitate the optimal placement of the screw.

SUMMARY OF THE PRESENT INVENTION

The present invention is a surgical screw and pedicle finder configured for use in spinal surgery. The screw is equipped with a tip which is configured to pivot about a pivot point. The pivot point preferably enables a range of 360 degrees of pivot movement which is restricted to an acute angle. The pivoting tip of the present invention enables the screw to automatically find the path of least resistance through the bone of the patient as it is placed during the procedure. Similarly, the pedicle finder of the present invention is equipped with a pivot point configured to facilitate the pivoting of a tip of the pedicle finder to assist in the preparation and placement of the screw during the surgical procedure.

The following brief and detailed descriptions of the drawings are provided to explain possible embodiments of the present invention but are not provided to limit the scope of the present invention as expressed herein this summary section.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

The present invention will be better understood with reference to the appended drawing sheets, wherein.

DETAILED DESCRIPTION OF THE PREFERRED EMBODIMENT

Figure 1:
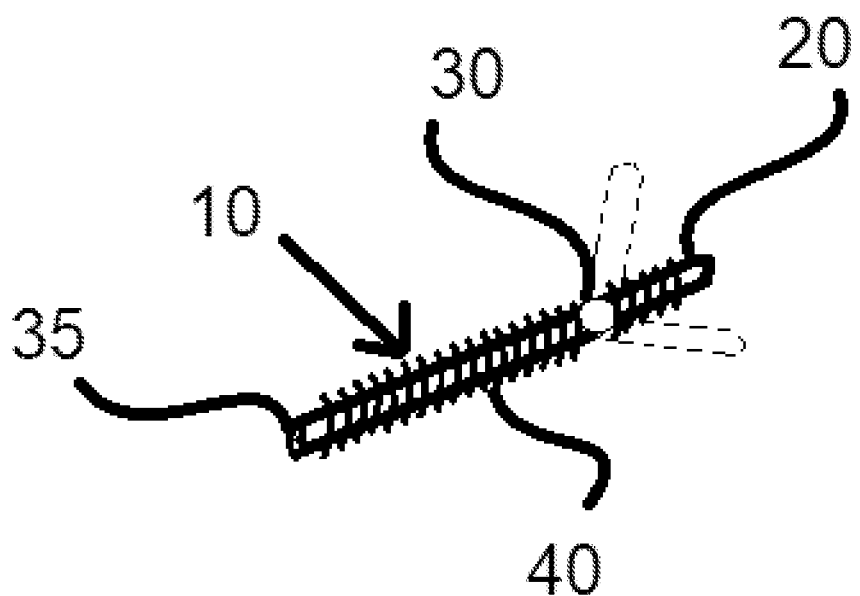
FIG. 1 depicts a view of the apparatus of the present invention as seen from the front.

The present specification discloses one or more embodiments that incorporate the features of the invention. The disclosed embodiment(s) merely exemplify the invention. The scope of the invention is not limited to the disclosed embodiment(s).

References in the specification to "one embodiment," "an embodiment," "an example embodiment," etc., indicate that the embodiment described may include a particular feature, structure, or characteristic, but every embodiment may not necessarily include the particular feature, structure or characteristic. Moreover, such phrases are not necessarily referring to the same embodiment, Further, when a particular feature, structure, or characteristic is described in connection with an embodiment, it is submitted that it is within the knowledge of one skilled in the art to effect such feature, structure, or characteristic in connection with other embodiments whether or not explicitly described.

The present invention is a surgical screw apparatus configured for use in spinal surgery. The apparatus is equipped with a body (10) which is cylindrical, a tip (20) which is conical, a pivot point (30) which is preferably a ball-and-socket type pivot point, a head (35) being the very end opposite from the tip (20), and threads (40). The pivot point (30) is disposed in communication with the tip (20) and the body (10), and is preferably outfitted with a ball-and-socket joint. The tip (20) is disposed on a first end and the head (35) is disposed on a second end of the body (10). The head (35), per convention, is equipped with a slot, cross indentation, square, torx, or similar conventional connection point.

The entirety of the body (10) and tip (20) are preferably equipped with a hollow tunnel (50) to facilitate the passage of a guide wire (60) which is used to stabilize the movement of the tip (20) if needed, preventing the tip from changing direction when not desired. It should be noted that, if sufficient tension is applied to the guide wire (60) to prevent motion of the tip (20) about the pivot point (30), the apparatus of the present invention may perform as a traditional surgical screw.

The tip (20) of the present invention is preferably configured to pivot in a range of up to 360 degrees about the pivot point (30), however some embodiments may limit the degree to which the tip (20) may pivot to 75 degrees from the neutral centered position. It should be understood that the tip (20) may pivot at varying degrees, and is not preferably restricted to 360 degrees or 75 degrees. The threads (40) of the apparatus preferably extend across the entirety of the body (10) and tip (20). Some embodiments may exhibit threading solely on the body (10) of the apparatus, leaving the pivot point (30) and tip (20) portions without threads (40).

The apparatus of the present invention is preferably available in a variety of sizes. Namely, the thickness, as well as length of the apparatus may differ, and may be manufactured in accordance with the needs of the operation. For example, the envisioned range of lengths of the apparatus is from 6 mm to 140 mm, however other sizes may be fashioned if necessary. Similarly, the diameter of the apparatus preferably ranges from 3 mm to 12 mm. It is known that differently sized screws are used at different locations depending on the shape and size of each bone to be outfitted with the apparatus. The tip (20) is preferably approximately 5 mm in length but may also vary in diameter and length depending on the overall size of the screw. It is envisioned that the preferred embodiment of the present invention exhibits a tip (20) which is pointed and follows the general shape and size of the body (10) of the apparatus.

The threads (40) of the present invention may be present in an assortment of sizes per conventional screws used in the art. The threading is prone to vary and be dependent on the different parts of the spine to which the present invention is positioned.

It should be noted that the material composition of the components of the present invention is preferably titanium, a cobalt/chromium alloy, or a mixture; however other materials may be employed if other more prudent alternative alloys are developed.

Figure 2:
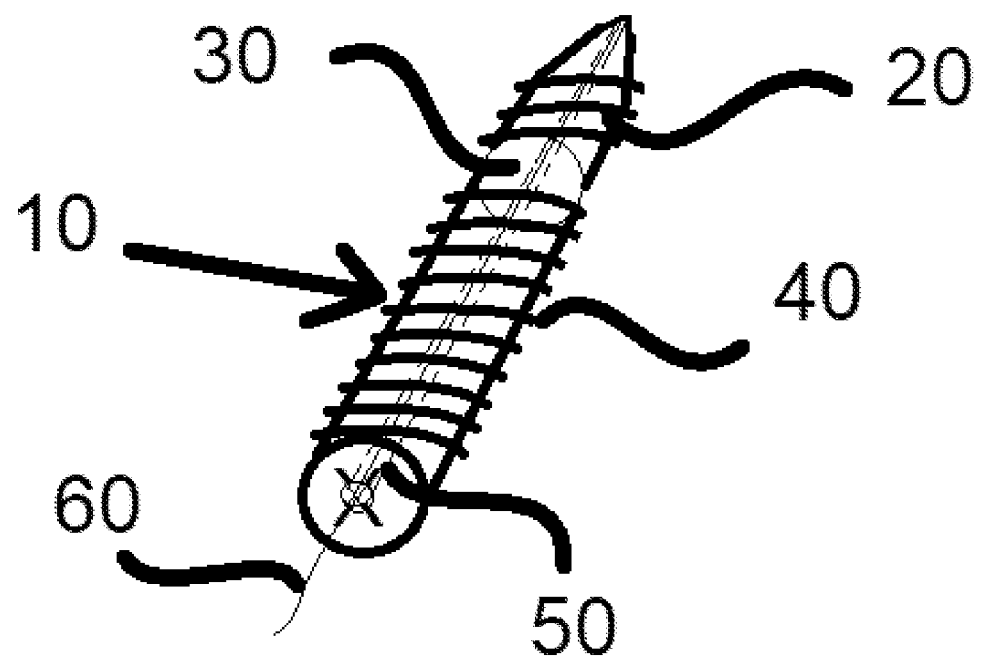
FIG. 2 exhibits a view of the apparatus of the present invention as seen from the top, detailing the hollow tunnel.
Figure 3:
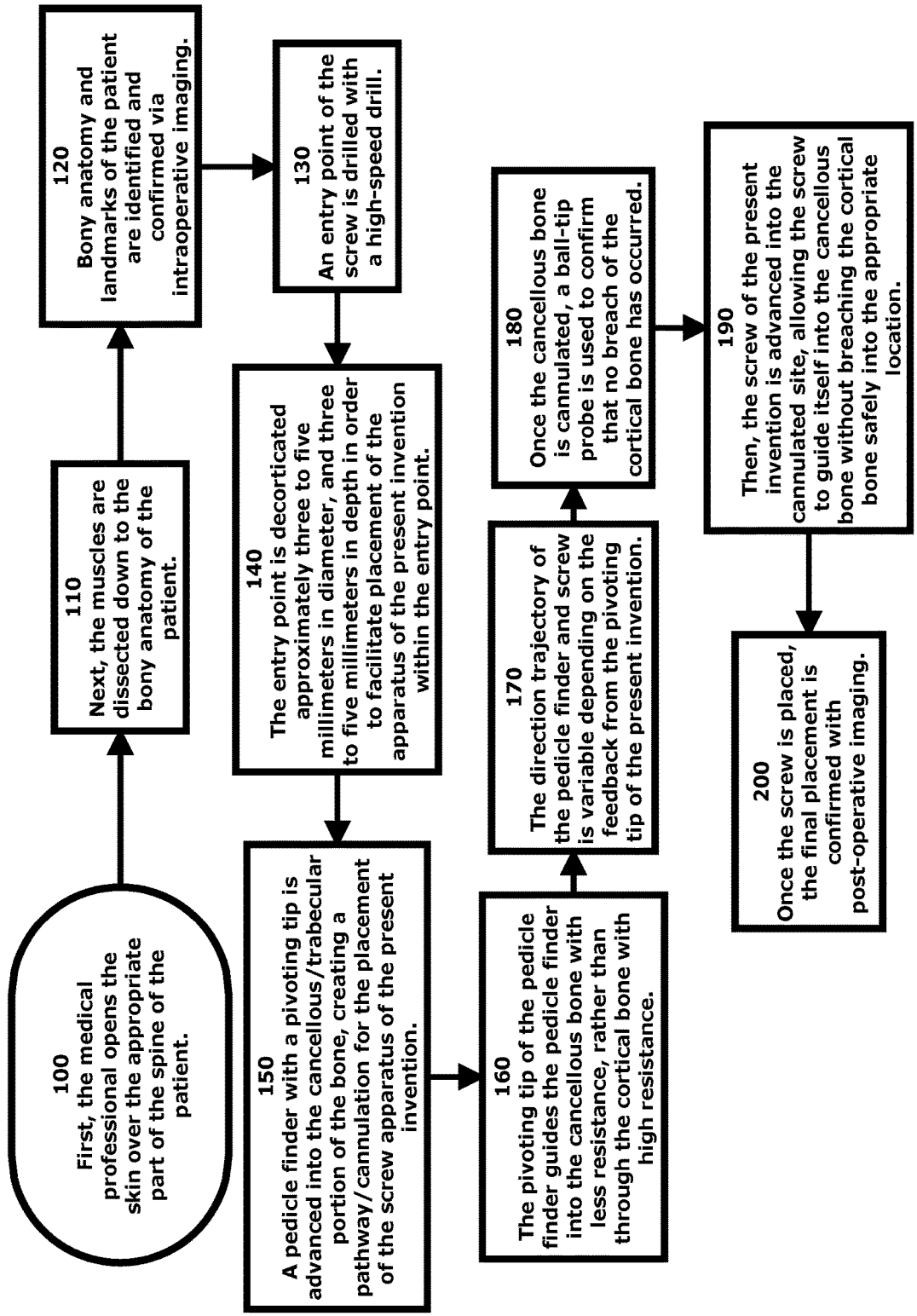
FIG. 3 shows a flow chart detailing the process of use of the present invention by a user.

The process of installation and use of the apparatus of the present invention, as shown in FIG. 2, is preferably as follows:
1. First, the medical professional opens the skin over the appropriate part of the spine of the patient. (100)
2. Next, the muscles are dissected down to the bony anatomy of the patient. (110)
3. Bony anatomy and landmarks of the patient are identified and confirmed via intraoperative imaging. (120)
4. An entry point of the screw is drilled with a high-speed drill. (130)
5. The entry point is decorticated approximately three to five millimeters in diameter, and three to five millimeters in depth in order to facilitate placement of the apparatus of the present invention within the entry point. (140)
6. A pedicle finder with a pivoting tip is advanced into the cancellous/trabecular portion of the bone, creating a pathway/cannulation for the placement of the screw apparatus of the present invention. (150) It should be noted that it is important for the pedicle finder to be equipped with a pivoting tip in order to avoid penetrating through the cortical bone of the patient.
7. The pivoting tip of the pedicle finder guides the pedicle finder into the cancellous bone with less resistance, rather than through the cortical bone with high resistance. (160)
8. The direction trajectory of the pedicle finder and screw is variable depending on the feedback from the pivoting tip of the present invention. (170)
9. Once the cancellous bone is cannulated, a ball-tip probe is used to confirm that no breach of the cortical bone has occurred. (180)
10. Then, the screw of the present invention is advanced into the cannulated site, allowing the screw to guide itself into the cancellous bone without breaching the cortical bone safely into the appropriate location. (190)
11. Once the screw is placed, the final placement is confirmed with post-operative imaging. (200)

It should be noted that the ball-and-socket joint configuration of the pivot point (30) of the present invention is subject to modification, and that similar forms of effective known pivot points may be used in alternate embodiments of the present invention. Similarly, it should be noted that the apparatus of the present invention may be equipped with a screw head, or alternatively may be headless, exhibiting one of a plurality of conventional head socket or slot designs.

Figure 4:
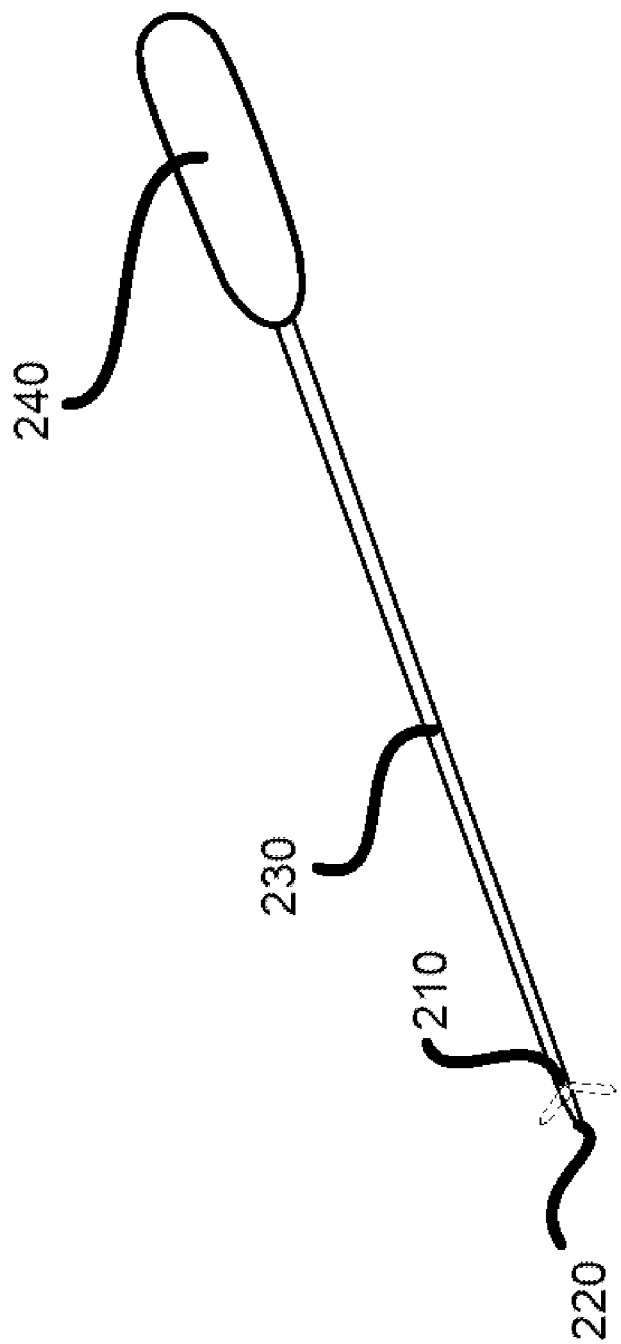
FIG. 4 exhibits a view of the pedicle finder accompanying apparatus of the present invention as seen from the side.
Figure 5:
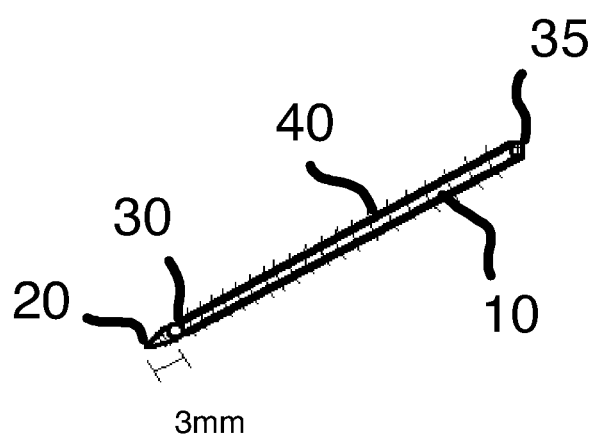
FIG. 5 depicts another view of the apparatus of the present invention, detailing the small conical tip in comparison to the generally non-conical body of the present invention.

Additionally, it should be understood that a pedicle finder of the present invention, as shown in FIG. 4, is an accompanying apparatus which is similarly equipped with a pivot point (210), a pivoting tip (220), and a shaft (230), and is configured to facilitate the positioning and piloting of the screw of the present invention into the needed location similar to conventional pedicle finders. Per conventional pedicle finders, the pedicle finder companion apparatus of the present invention is equipped with a handle (240) which is preferably ergonomically shaped for comfort.

It should be understood that the screw and pedicle finder of the present invention may be used in other orthopedic surgical procedures, and is not limited to spinal surgery. Similarly, it should be noted that the screw equipped with the pivot point (30) of the present invention may be used in other industries to allow better feedback and guidance during placement.

Further, it should be understood that the tip (20) is defined by a conical taper which begins at the pivot point (30) and ends at the narrow, pointed end of the apparatus. The nature of the pivot point (30) ensures rotation and pivoting of the tip (20) may be beyond 90 degrees in any direction. The tip (20) itself, is only three to five millimeters in length, and begins at the pivot point (30), when the tapering towards a point begins.

Having illustrated the present invention, it should be understood that various adjustments and versions might be implemented without venturing away from the essence of the present invention. Further, it should be understood that the present invention is not solely limited to the invention as described in the embodiments above, but further comprises any and all embodiments within the scope of this application.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

I claim:
1. A method of use for a surgical screw apparatus for use in a surgical procedure involving an insertion of the surgical screw apparatus into a single spinal bone of a patient by a medical professional comprising:
   opening the skin over the single spinal bone of the spine of the patient;
   dissecting muscles overlying the spine down to bony anatomy;
   identifying the bony anatomy and landmarks of the patient;

drilling an entry point into the single spinal bone for the surgical screw apparatus with a high-speed drill;

confirming via intraoperative imaging the bony anatomy and landmarks of the patient;

wherein the entry point is decorticated approximately three to five millimeters in diameter, and three to five millimeters in depth, enabling precise placement of the surgical screw apparatus within the entry point;

advancing a pivoting tip of the surgical screw apparatus into the cancellous/trabecular portion of the single spinal bone, creating a pathway/cannulation for the placement of the surgical screw apparatus;

wherein the pivoting tip ensures the cortical bone of the patient is not penetrated, following the path of least resistance;

the pivoting tip guiding the surgical screw apparatus into the cancellous bone with minimal resistance rather than going through the cortical bone with high resistance;

wherein the direction trajectory of the surgical screw apparatus is variable depending on the feedback from a pivoting tip of the screw;

using a ball-tip probe to confirm that the cortical bone has not been breached once the cancellous bone is cannulated;

advancing the surgical screw apparatus into the cannulated site, the pivoting tip of the surgical screw apparatus pivoting as a guide;

the surgical screw apparatus guiding itself into the cancellous bone without breaching the cortical bone via the pivoting tip of the surgical screw apparatus pivoting as a guide; and confirming the final placement of the surgical screw apparatus with post-operative imaging.

2. The method of claim 1, wherein the pivoting tip of the surgical screw apparatus pivots about a pivot point.

3. The method of claim 2, wherein the pivot point is a ball and socket joint.

4. The method of claim 3, wherein the surgical screw apparatus is equipped with a slot on a head end opposite the pivoting tip of the surgical screw apparatus.

5. The method of claim 4, wherein the head end is configured to facilitate turning of the surgical screw apparatus with an external tool.

6. The method of claim 3, wherein the surgical screw apparatus is headless.

7. The method of claim 6, wherein the surgical screw apparatus is equipped with threading extending until the pivot point.

8. The method of claim 7, wherein the surgical screw apparatus has an elongated body ranging between 6 mm and 140 mm in length.

9. The method of claim 7, wherein the surgical screw apparatus has a diameter between 3 mm and 12 mm.

10. The method of claim 7, wherein the pivoting tip of the surgical screw apparatus is approximately 5 mm in length.

11. The method of claim 7, wherein the pivoting tip of the surgical screw apparatus is pointed.

12. The method of claim 7, wherein the threading of the surgical screw apparatus ends prior to the pivot point pivoting tip of the surgical screw apparatus.

13. The method of claim 3 wherein the pivot point of the surgical screw apparatus limits the degree to which the tip of the surgical screw apparatus may pivot to 75 degrees from a central axis of the surgical screw apparatus; and wherein the tip of the surgical screw apparatus is forward of the pivot point and is domed.

14. The method of claim 1, further comprising:

inserting a guide wire into a hollow tunnel of the surgical screw apparatus; and using the guide wire to stabilize the movement of the pivoting tip, preventing the tip from changing direction when not desired.

15. The method of claim 14, wherein the surgical screw apparatus is composed of a metallic alloy.

16. The method of claim 15, wherein the metallic alloy is one of the following: titanium, cobalt/chromium, or a mixture of titanium and cobalt/chromium.

* * * * *